United States Patent [19]

Schoenmakers et al.

[11] Patent Number: 5,798,105
[45] Date of Patent: Aug. 25, 1998

[54] DNA ENCODING A PLASMODIUM 16KD PROTEIN

[75] Inventors: Johannes Geradus Ghislain Schoenmakers, Mook; Rudolph Nicolaas Hendrik Konings, Guijk; Inge Irma Maria Dominique Moelans, Nijmegen, all of Netherlands

[73] Assignee: University of Nijmegan, Netherlands

[21] Appl. No.: 450,065

[22] Filed: May 25, 1995

Related U.S. Application Data

[63] Continuation of Ser. No. 949,645, Dec. 4, 1992, abandoned.

[30] Foreign Application Priority Data

Jun. 6, 1990 [GB] United Kingdom ............... 9012580

[51] Int. Cl.⁶ .................. A61K 39/015; C12P 21/06; C12N 15/00; C07H 21/04
[52] U.S. Cl. ............. 424/272.1; 435/69.1; 435/69.3; 435/172.3; 435/252.3; 435/320.1; 530/350; 536/23.1; 536/23.4; 536/23.7; 935/12; 935/47; 935/55; 935/65
[58] Field of Search ................. 435/69.1, 69.3, 435/172.3, 320.1, 252.3; 530/350; 536/23.1, 23.4, 23.7; 935/12, 47, 55, 65; 424/272.1

[56] References Cited

PUBLICATIONS

Brown KW. Nature 311(27):300. 1984.
Good MF. Immunology Today 13(4):126–130, 1992. (Comment by Eleanor Riley).

*Primary Examiner*—James C. Housel
*Assistant Examiner*—Verlene Ryan
*Attorney, Agent, or Firm*—Kirk Baumeister; Charles M. Kinzig; Edward T. Lentz

[57] ABSTRACT

A DNA encoding a 16 kD protein capable of inducing an immune response protective against human malarial infection caused by *Plasmodium falciparum*, and to the cloning and expression of a gene encoding the said protein. The invention further relates to novel vaccines comprising the said protein and to their use in the vaccination of humans at risk from malaria.

7 Claims, 1 Drawing Sheet

FIGURE 1

```
                                                      ttttatttt attttt 17 ttta ttttttattt tttttctttt gccatttttc tatttatact ttcttcaac 1 met asn ile arg lys phe ile pro ser leu ala leu met leu ile
 71 ATG AAT ATT CGA AAG TTC ATA CCA TCT TTA GCT TTA ATG CTT ATA 16 phe phe ala phe ala asn leu val leu ser asp ala asn asp lys
116 TTC TTC GCT TTT GCA AAC CTG GTA TTA TCA GAT GCA AAT GAC AAA 31 ala lys lys pro ala gly lys gly ser pro ser thr leu gln thr
161 GCA AAA AAG CCC GCT GGA AAA GGA TCC CCT TCA ACT TTG CAA ACC 46 pro gly ser ser ser gly ala ser leu his ala val gly pro asn
206 CCA GGA AGT TCT TCA GGT GCC TCT CTT CAT GCT GTT GGA CCT AAT 61 gln gly gly leu ser gln gly leu ser gly lys asp ser ala asp
251 CAA GGT GGA CTA TCT CAA GGT CTT TCT GGA AAA GAT TCT GCT GAC 76 lys met pro leu glu thr gln leu ala ile glu glu ile lys ser
296 AAA ATG CCT TTA GAA ACT CAG CTA GCT ATA GAA GAA ATC AAG AGC 91 leu ser asn met leu asp lys lys thr thr val asn arg asn leu
341 TTA TCC AAT ATG TTA GAT AAA AAA ACG ACA GTT AAC AGA AAC TTA 106 ile ile ser thr ala val thr asn met ile met leu ile ile leu
386 ATC ATA AGT ACT GCT GTC ACA AAT ATG ATC ATG TTG ATC ATA TTA 121 ser gly ile val gly phe lys val lys lys thr lys asn ala asp
431 TCT GGT ATA GTT GGA TTT AAA GTT AAA AAA ACG AAG AAC GCA GAT 136 asp asp lys gly asp lys asp lys asp lys asp asn thr asp glu
476 GAT GAT AAA GGA GAT AAC GAT AAG GAC AAG GAT AAT ACA GAT GAA 151 gly asp glu gly asp asp ser ***
521 GGA GAC GAA GGA GAT GAT TCT taa atgta tatatatata tatatatata 570
tatttattta tttatttaaa tatttatata tatatatata ttatatatat aata 615 ttttat aatttt
```

DNA ENCODING A PLASMODIUM 16KD PROTEIN

This is a continuation of application Ser. No. 07/949,645, filed Dec. 4, 1992, now abandoned.

This invention relates to a novel protein capable of inducing an immune response protective against human malarial infection caused by *Plasmodium falciparum*, and to the cloning and expression of a gene encoding the said protein. The invention further relates to novel vaccines comprising the said protein and to their use in the vaccination of humans at risk from malaria.

Human malaria is caused by a parasite of the genus Plasmodium. There are four species of Plasmodium known to infect man: *P. falciparum*, *P. vivax*, *P. malariae*, and *P. ovale*. The most severe forms of human malaria are caused by *P. falciparum*, and *P. vivax*. *P. falciparum* is the most prevalent.

The malarial parasite is transmitted by mosquitoes to man in the form of a sporozoite, which migrates to the liver, multiplies within hepatocytes and emerges to initiate a cyclical growth in erythrocytes. The merozoite-stage parasite, which is released at the end of each cycle, rapidly reinvades red blood cells. A few merozoites develop into the sexual-stage parasite (male and female gametocytes) which, after being ingested in a blood meal, complete their life cycle in the female Anopheles mosquito, concluding in the production of sporozoite offspring.

Malaria is a debilitating disease, and it would therefore clearly be desirable to develop a vaccine based on surface antigens present in one or more of the stages of the parasite, which stages are immunologically distinct from one another. However, efforts in this direction have so far met with limited success.

It has been shown that mammals, including man, have been protected against Plasmodium challenge when vaccinated with irradiated sporozoites (Clyde et al., *Am J Trop Med Hyg*, 24: 397 (1975), Nussenzweig et al., *Phil Tran R Soc Lond B*, 307: 117–28 (1984)). This method, while effective, is limited due to the difficulty of cultivating sporozoites.

The sporozoites express a species-specific surface protein, the circumsporozoite (CS) protein, which was first identified in *P. berghei*, a parasite of rodents. Monoclonal antibodies to this protein completely protected mice from challenge with infected mosquitoes (Potocnjak et al., *J Exp Med*, 151: 1504–13 (1980)).

Research based on the CS protein has been widely reported (see, for example, *Science*, 225: 593–9 and 628–9 (1984), U.S. Pat. No. 4,707,357, *Science*, 230: 815–18 (1985), *Science*, 228: 958–62 (1985), PCT/WO86/01721 and *Lancet*, I: 1277–81 (1987)). However, a vaccine based on the CS protein or a subunit thereof has never been commercialized, and clinical trials have proved disappointing ("Malaria vaccines: The Failed Promise", *Science*, 247: 402–3 (1990)).

Recent data has shed some doubts about the usefulness of the CS protein as a potential vaccine candidate: Poor immunogenicity in man, strong genetic restriction (as shown in mice) of the immune response to the antigen and polymorphism of immunologically relevant sequences suggest that this protein, without alternative modification, may not be developed into an effective anti-sporozoite and/or anti-liver stage vaccine. Therefore, the identification of new exoerythrocytic antigens that may induce protective immunity against the sporozoite and/or hepatic stage parasite is today recognized as an important priority in the field of malaria vaccine development (*Parasitology Today*, 6: 3, 64–65 (1990) and *Immunology Today*, 9: 351–355 (1988)).

An alternative, or additional, strategem would be to produce sexual stage vaccines that would induce antibodies, which, when ingested in a bloodmeal containing sexual parasites, would prevent infection of mosquitoes and hence transmission. Although such a transmission blocking vaccine will not protect the vaccinated individual from infection, it would reduce when combined with a sporozoite and/or asexual erythrocytic stage vaccine the chance of transmission of vaccine-induced mutants resistant to either one of these vaccines.

It has been suggested that polymorphism may be less likely in sexual stage proteins since these are expressed only when the parasite enters the mosquito and are therefore not seen by the human immune system which is perhaps the chief pressure to evolutionary change in sporozoites.

Transmission blocking immunity has successfully been induced by immunisation with extracellular gametes in several species. In *Plasmodium falciparum*, three stage-specific antigens (25, 45/48 and 230 kDa) have been identified against which monoclonal antibodies block transmission. These antigens represent surface proteins which are expressed during different phases of the sexual stage of the parasite. Kaslow et al (*Nature*, 333, 74–76 (1988)) have recently cloned the gene encoding the 25 kDa protein. The latter protein represents a surface protein on zygotes and ookinetes of *P. falciparum*.

Cloning of other *P. falciparum* genes involved in the induction of transmission blocking immunity has not been carried out so far, mainly because of problems in obtaining sufficient quantities of parasites and purified protein needed for peptide sequencing.

We have adopted a novel cloning strategy which does not rely on the availability of a peptide sequence to construct hybridization probes. Instead, a subtractive hybridization technique was used based on the observation that the sexual stage surface antigens are probably not expressed in the asexual blood stages.

A cDNA library was constructed from total gametocyte RNA obtained from *P. falciparum* NF54 and screened for the presence of sexual stage-specific encoding sequences by hybridization with radiolabelled single stranded cDNA constructed from RNA isolated from sexual and asexual blood stages of the parasite. Those clones which hybridized with the asexual cDNA probes were eliminated.

As a result, we have identified a novel gene which is expressed in the sexual stages of the parasite. Analysis of the deduced primary structure reveals that the gene codes for a protein of 16 kDa which has all the characteristics of a surface protein. Immuno-electron microscopy studies have clearly demonstrated the presence of the 16 kDa protein in the membrane of gametocytes and gametes. In view of these aspects this feature makes it a potential component of a transmission blocking malaria vaccine.

Surprisingly, the product of the Pfs16 gene has also been identified on the surface of *P. falciparum* sporozoites. Antibodies prepared against a synthetic peptide of Pfs16 as well as antibodies prepared against recombinant fusion proteins of Pfs16 not only recognize the 16 kDa protein in sporozoite protein extracts by Western blotting but recent immuno-electron microscopy studies have also demonstrated its presence on the surface of sporozoites.

The 16 kDa antigen of *P. falciparum* (or recombinant DNA-contructs thereof) therefore has the potential to elicit a dual protective immune response against the sporozoite and exoerythrocytic stage parasite as well as against its sexual forms.

Accordingly, the present invention provides the 16 kDa protein having the sequence shown below, and immunogenic derivatives (including mutants) thereof.

The term "immunogenic derivative" encompasses any molecule such as a truncated or other derivative of the protein which retains the ability to induce an immune response to the protein following internal administration to a human. Such other derivatives can be prepared by the addition, deletion, substitution, or rearrangement of amino acids or by chemical modifications thereof.

Immunogenic fragments of the protein, which may be useful in the preparation of subunit vaccines, may be prepared by expression of the appropriate gene fragments or by peptide synthesis, for example using the Merrifield synthesis (The Peptides, Vol 2., Academic Press, N.Y., page 3).

The immunogenic derivative of the invention can be a hybrid, that is, a fusion polypeptide containing additional sequences which can carry one or more epitopes for other Plasmodium immunogens, or other non-Plasmodium immunogens. Alternatively, the immunogenic derivative of the invention can be fused to a carrier polypeptide such as Hepatitis B surface or core antigen or to another carrier which has immunostimulating properties, as in the case of an adjuvant, or which otherwise enhances the immune response to the 16 kDa protein or derivative thereof, or which is useful in expressing, purifying or formulating the 16 kDa protein or derivative thereof.

The invention also extends to the 16 kDa protein or immunogenic derivative thereof when chemically conjugated to a macromolecule using a conventional linking agent such as glutaraldehyde (Geerlings et al, (1988) J. Immunol. Methods, 106, 239–244).

A further aspect of the invention provides a process for the preparation of the 16 kDa protein or an immunogenic derivative thereof, which process comprises expressing DNA encoding said protein or derivative thereof in a recombinant host cell and recovering the product, and thereafter, optionally, preparing a derivative thereof.

A DNA molecule comprising such coding sequence forms a further aspect of the invention and can be synthesized by standard DNA synthesis techniques, such as by enzymatic ligation as described by D. M. Roberts et al in Biochemistry 1985, 24, 5090–5098, by chemical synthesis, by in vitro enzymatic polymerization, or by a combination of these techniques.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°–37° C., generally in a volume of 50 µl or less. Enzymatic ligation of DNA fragments may be carried out using a DNA ligase such as T4 DNA ligase in an appropriate buffer, such as 0.05M Tris (pH 7.4), 0.01 M $MgCl_2$, 0.01 M dithiothreitol, 1 mM spermidine, 1 mM ATP and 0.1 mg/ml bovine serum albumin, at a temperature of 4° C. to ambient, generally in a volume of 50 µl or less. The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie Weinheim (1982) or in other scientific publications, for example M. J. Gait, H. W. D. Matthes. M. Singh, B. S. Sproat, and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society,1983, 105, 10 661; N. D. Sinha, J. Biernat, J. McMannus, and H. Koester, Nucleic Acids Research, 1984, 12, 4539; and H. W. D. Matthes et al., EMBO Journal, 1984, 3, 801.

Alternatively, the coding sequence can be derived from *P. falciparum* mRNA, using known techniques (e.g. reverse transcription of mRNA to generate a complementary cDNA strand), and commercially available cDNA kits.

The invention is not limited to the specifically disclosed sequence, but includes all molecules coding for the 16 kDa protein or an immunogenic derivative thereof, as described above.

DNA polymers which encodes mutants of the 16 kDa protein may be prepared by site-directed mutagenesis of the cDNA which codes for the 16 kDa protein by conventional methods such as those described by G. Winter et al in Nature 1982, 299, 756–758 or by Zoller and Smith 1982; Nuc. Acids Res., 10, 6487–6500, or deletion mutagenesis such as described by Chan and Smith in Nucl. Acids Res., 1984, 12, 2407–2419 or by G. Winter et al in Biochem. Soc. Trans., 1984, 12, 224–225.

The process of the invention may be performed by conventional recombinant techniques such as described in Maniatis et. al., Molecular Cloning—A Laboratory Manual; Cold Spring Harbor, 1982-1989.

In particular, the process may comprise the steps of:
i) preparing a replicable or integrating expression vector capable, in a host cell, of expressing a DNA polymer comprising a nucleotide sequence that encodes said 16 kDa protein or an immunogenic derivative thereof;
ii) transforming a host cell with said vector;
iii) culturing said transformed host cell under conditions permitting expression of said DNA polymer to produce said protein; and
iv) recovering said protein.

The term 'transforming' is used herein to mean the introduction of foreign DNA into a host cell by transformation, transfection or infection with an appropriate plasmid or viral vector using e.g. conventional techniques as described in Genetic Engineering; Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest.

The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment encode the desired product, such as the DNA polymer encoding the 16 kDa protein, or fragments thereof, under ligating conditions.

Thus, the DNA polymer may be preformed or formed during the construction of the vector, as desired.

The choice of vector will be determined in part by the host cell, which may be prokaryotic or eukaryotic. Suitable vectors include plasmids, bacteriophages, cosmids and recombinant viruses.

The preparation of the replicable expression vector may be carried out conventionally with appropriate enzymes for restriction, polymerisation and ligation of the DNA, by procedures described in, for example, Maniatis et al cited above.

The recombinant host cell is prepared, in accordance with the invention, by transforming a host cell with a replicable expression vector of the invention under transforming conditions. Suitable transforming conditions are conventional and are described in, for example, Maniatis et al cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al, Proc. Nat. Acad. Sci., 1973, 69, 2110) or with a solution comprising a mixture of RbCl, $MnCl_2$ potassium acetate and glycerol, and then with 3-[N-morpholino]-propane-sulphonic acid, RbCl and glycerol. Mammalian cells in culture may be transformed by calcium co-precipitation of the vector DNA onto the cells. The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 45° C.

The product is recovered by conventional methods according to the host cell. Thus, where the host cell is bacterial, such as *E. coli* it may be lysed physically, chemically or enzymatically and the protein product isolated from the resulting lysate. Where the host cell is mammalian, the product may generally be isolated from the nutrient medium or from cell free extracts. Conventional protein isolation techniques include selective precipitation, absorption chromatography, and affinity chromatography including a monoclonal antibody affinity column.

Preferably, the host cell is *E. coli*. Alternatively, the expression may be carried out in insect cells using a suitable vector such as the Baculovirus. In a particular aspect of this invention, the protein is expressed in Lepidoptera cells to produce immunogenic polypeptides. For expression of the protein in Lepidoptera cells, use of a baculovirus expression system is preferred. In such system, an expression cassette comprising the protein coding sequence, operatively linked to a baculovirus promoter, typically is placed into a shuttle vector. Such vector contains a sufficient amount of bacterial DNA to propagate the shuttle vector in *E. coli* or some other suitable prokaryotic host. Such shuttle vector also contains a sufficient amount of baculovirus DNA flanking the desired protein coding sequence so as to permit recombination between a wild-type baculovirus and the heterologous gene.

The recombinant vector is then cotransfected into Lepidoptera cells with DNA from a wild-type baculovirus. The recombinant baculoviruses arising from homologous recombination are then selected and plaque purified by standard techniques. See Summers et al., *TAES Bull* (Texas Agricultural Experimental Station Bulletin) NR 1555, May, 1987.

A process for expressing the CS protein in insect cells is described in detail in U.S. Ser. No. 287,934 of SmithKline RIT (WO/US 89/05550).

Production in insect cells can also be accomplished by infecting insect larvae. For example, the protein can be produced in *Heliothis virescens* caterpillars by feeding the recombinant baculovirus of the invention along with traces of wild type baculovirus and then extracting the protein from the hemolymph after about two days. See, for example, Miller et al., PCT/WO88/02030.

The novel protein of the invention may also be expressed in yeast cells as described for the CS protein in EP-A-0 278 941.

The vaccine of the invention comprises an immunoprotective amount of the 16 kDa protein or an immunogenic derivative thereof. The term "immunoprotective" refers to the amount necessary to elicit an immune response against a subsequent *P. falciparum* challenge such that disease is averted or mitigated, and/or transmision of the disease is blocked or delayed. In the vaccine of the invention, an aqueous solution of the protein can be used directly. Alternatively, the protein, with or without prior lyophilization, can be mixed or absorbed with any of the various known adjuvants. Such adjuvants include, but are not limited to, aluminium hydroxide, muramyl dipeptide and saponins such as Quil A, 3D-MPL (3Deacylated monophosphoryl lipid A), or TDM. As a further exemplary alternative, the protein can be encapsulated within microparticles such as liposomes. In yet another exemplary alternative, the protein can be conjugated to an immuostimulating macromolecule, such as killed Bordetella or a tetanus toxoid.

Vaccine preparation is generally described in *New Trends and Developments in Vaccines*, Voller et al. (eds.), University Park Press, Baltimore, Md., 1978. Encapsulation within liposomes is described by Fullerton, U.S. Pat. No. 4,235,877. Conjugation of proteins to macromolecules is disclosed, for example, by Likhite, U.S. Pat. No. 4,372,945 and Armor et al., U.S. Pat. No. 4,474,757.

Use of Quil A is disclosed by Dalsgaard et al., *Acta Vet Scand*, 18: 349 (1977).

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each dose will comprise 1–1000 µg of protein, prefer ably 1–200 µg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists.

A further aspect of the invention provides a method of preventing or mitigating malarial infections in man, and/or blocking transmission of the malaria parasite, which method comprises administering to a subject in need thereof an immunogenically effect amount of the 16 kDa protein or of an immunogenic derivative thereof, or of a vaccine in accordance with the invention.

The examples which follow are illustrative but not limiting of the invention. Restriction enzymes and other reagents were used substantially in accordance with the vendors' instructions.

EXAMPLE 1
Isolation and Nucleotide Sequencing of the Pfs16 Gene

Mature *P. falciparum* (NF54) gametocytes were produced in a semiautomated suspension culture system (Ponnudurai et al., 1983). Fourteen days after cultivation, infected erythrocytes were harvested by centrifugation for 5 min. at 560×g. Following induction of gametogenesis (Vermeulen et al., 1983) the macrogametes/zygotes and gametocytes were separately recovered by centrifugation through a discontinuous Nycodenz (Nyegaard, Oslo) gradient as described by Vermeulen et al. (1983). After lysis of these cells in 100 mM NaCl, 50 mM Tris-HCl pH7.2, 50 mM EDTA, 0.2% SDS and 2% Triton-X100, the RNA was purified by phenol/chloroform extraction and centrifugation through a cushion of 5.7 M CsCl in 30 mM NaAc, pH 6.8 and 50 mM EDTA as described by Maniatis et al. (1982).

A cDNA library was constructed from total gametocyte RNA obtained from *Plasmodium falciparum* NF54. The cDNA was synthesized by oligo(dT) primed first-strand synthesis and RNase H-DNA polymerase I mediated second strand synthesis (Gubler and Hoffmann, 1983). Following homopolymer tailing with dGTP the cDNA was annealed into the oligo(dC)-tailed SstI-site of plasmid pPLc24511. Vector pPLc24511 is a derivative of plasmid pPLc245 (Remaut et al., 1983) in which the 221 bp SalI/RsaI restriction fragment has been replaced by the SalI/PvuII fragment of M13mp11 DNA. After transformation into *E.coli* MC1061 (Casadaban and Cohen, 1980) about 25.000 transformants were obtained. The cDNA library thus constructed was screened for the presence of sexual stage-specific encoding sequences by in situ hybridization with $^{32}$p-labelled single-stranded cDNA, prepared by oligo(dT) priming of RNA isolated from gametocytes, macrogametes/zygotes and asexual bloodstages of the NF54 parasite. Clones were identified which only hybridized with macrogamete/zygote and gametocyte cDNA probes. One of the clones—GB8—contained part of the sequence shown below. The inserted fragment was isolated, labelled with $^{32}$p and then used to screen a lambda-gt11 cDNA library of total gametocyte RNA from *P. falciparum* NF54. The construction of this library has been published (Wesseling et al., 1989). One of these phage clones (GB8c) contained the Pfs16 DNA sequence shown below.

Northern hybridization analysis of total RNA from *P. falciparum* asexual bloodstages, gametocytes and macrogametes/zygotes revealed that clone GB8c contained a gene which is expressed as a single mRNA species of about 1400 bp in gametocytes and macrogametes/zygotes. Hybridization on RNA from the asexual bloodstages was virtually absent or only very weak.

For Northern hybridization, 3 µg of total RNA (isolated from either asexual bloodstages, gametocytes or gametes/zygotes) was loaded on a 1% agarose gel containing 2.2M formaldehyde. The gel was electrophoresed in 25 mM NaPO$_4$ buffer (pH 7.0) and RNA was transferred to nitrocellulose (Schleicher and Schuell) in 20×SSPE. Hybridization of the blots was carried out at 42° C. for 16 hours in 50 mM NaPO$_4$ (pH 6.5), 0.8M NaCl, 50% formamide, 1 mM EDTA, 0.1% SDS, 2.5×Denhardt's solution, 50 µg/ml denatured salmon sperm DNA and 500 µg/ml yeast RNA. The blots were washed at high stringency (0.1% SDS, 65° C.).

Probes of high specific radioactivity were prepared by in vitro transcription of the appropriate restriction fragments which had previously been ligated into the polylinker of pGEMblue.

For nucleotide sequence analysis the appropriate DNA fragments were digested from the selected recombinant plasmids and subcloned into M13mp10/mp11 vectors (Gene, 26: 101–106 (1983)). The nucleotide sequence was established according to the dideoxy sequencing strategy as originally developed by Sanger (Sanger et al., 1977).

The nucleotide sequence of the Pfs16 coding region an flanking regions is shown in FIG. 1 and SEQ. I.D. No. 1 attached. Nucleotides are numbered relative to the A of the ATG initiation codon. The deduced amino acid sequence is indicated above the nucleotide sequence and is numbered according to the numbering system proposed by Lu and Elzinga (1977) and is shown in SEQ. I.D. No. 2. The solid box represents the amino acid sequence of the synthetic peptide of Example 6.

The deduced amino acid sequence comprises a signal sequence at the N-terminus and a membrane anchor sequence followed by a hydrophilic sequence at the C-terminus. The sequence lacks the amino acids Cys, Trp and Tyr. Within the protein sequence no potential N-glycosylation sites (Asn-X-Ser/Thr) were detected. Computer search analysis at the DNA level (EMBL nucleotide database; release 12) as well as the protein level (NBRF/PIR protein database; release 12) indicated that the Pfs16 gene and its derived protein sequence have no significant similarity with any DNA sequence or protein sequence known so far.

EXAMPLE 2
Expression of Gene Pfs16 in COS-cells

Gene Pfs16 has been inserted immediately downstream (BstX1 site) of the CMV promoter in the vector plasmid CDM8. After selection of the appropriate recombinant plasmid the transient production in COS cells (derived from monkey kidney cells) of the protein (Pfs 16kDa) that is encoded by gene Pfs16 cells was studied with an immune fluorescence assay (IFA). From these studies it could be concluded that after transfection on the surface of the COS cells an antigen could be detected that specifically reacted with antisera raised against (recombinant) 16 kDa protein or fragments thereof.

EXAMPLE 3
Expression of Gene Pfs16 in Insect Cells

To express the Pfs16 gene in tissue culture cells of the fall army worm *Spodoptera frugiperda* (Sf9 cells) use has been made of the expression system derived from the baculovirus AcMNPV. As transfer vector, plasmid pJVP10.Z.Pfs16 was used. This plasmid is a derivative of the positive selection (β-galactosidase) vector pJVP10.Z and constructed by insertion of a blunt ended PCR fragment (Vialgrd et al 1990) that, encompasses the complete Pfs16 gene plus flanking sequences (i.e. 4 nucleotides at its 5' end and 3 nucleotides at the 3' end), in its unique NheI site made blunt ended with T4 DNA polymerase. This site is located immediately downstream of the polyhedrin promoter.

After selection and cloning of the recombinant AcMNPV10.Z.-Pfs16 virus containing the Pfs16 gene it was further propagated. Subsequently it was studied whether after infection of Sf9 cells with the recombinant virus 16kDa protein was made.

This indeed turned out to be the case. With the aid of immunofluorescense studies it could be demonstrated that the protein is primarly located on the surface of the Sf9 cell. Secretion of the Pfs16 protein was not observed. Immunological screening of Western blots prepared from total cell extracts of AcMNPV-10Z.Pfs16 infected cells has demonstrated that in the Sf9 cells at least three gene Pfs16 specific proteins ar made. The largest one is probably the unprocessed precursor of the (middle) protein that co-migrates with the Pfs16 protein present in gametocytes of *Plasmodium falciparum*. The nature of the smallest protein is not known. Judged from its electrophoretic mobility we conclude that it is larger than the signal peptide that is cleaved off from the precursor protein of the 16 kDa protein during its insertion in the host cell membrane. Surprisingly a similar set of proteins with identical molecular weights has also been observed after expression of the complete Pfs16 gene in *E.coli*.

EXAMPLE 4
Construction of Recombinant Vaccinia Virus Expressing the PFS16 Gene

The complete coding sequence of the Pfs16 gene was cloned into the unique SmaI restriction enzyme cleavage site of the vaccinia transfection plasmid pSC11 (1), yielding recombinant plasmid pSC11:Pfs16.

In this construct, the Pfs16 gene is under the transcriptional control of the vaccinia virus 7.5 promotor (1).

To obtain a recombinant vaccinia virus expressing the Pfs16 gene, standard published methods were used (2) Briefly, CV1 cells (ATCC # CCL70) were infected with wild vaccinia virus (strain WR), then transfected with plasmid pSC11:Pfs16. A virus stock obtained from these infected cells was used to infect a monolayer of RAT-2 (TK⁻) cells (ATCC # CRL1764), in the presence of 5-bromodeoxyuridine (BUdR). Recombinant viruses were selected as TK⁻, βGal⁺ lysis plaques. They were further subjected to three cycles of plaque purification on RAT-2 cells, again using the double TK⁻, βGal⁺ selection. The purified recombinant virus obtained was designated vSC11:Pfs16.

To demonstrate expression of the Pfs16 gene by this recombinant virus, CV1 and BHK21 (ATCC # CC110) cells were infected with vSC11:Pfs16 or with a control recombinant virus, vSC11, that does not contain the Pfs16 gene coding sequence. Sixteen to 48 hours following infection, the cells were harvested, lysed in PAG/SDS loading buffer, and the cell extracts were analysed by immunoblot. The blots were reacted with a rabbit anti-serum (K37S8) raised against a purified, E. coli produced, recombinant 16kDa protein. The results of this analysis demonstrate that CV1 and BHK21 cells infected with virus vSC11:Pfs16 synthesize the 16kDa antigen.

References

1. CHAKRABARTI S., BRACHLING K. and MOSS B. (1985). "Vaccinia Virus Expression vector: coexpression of β. Galactosidase Provides Visual Screening of Recombinant Virus Plaques".

MOL AND CELL. BIOL. 5: 3403–3409

2. MACKETT M., SMITH G. L., and MOSS B. (1984). "General Method for Production and Selection of Infectious Vaccinia Virus Recombinants Expression Foreign Genes".

J. Virol. 49: 857–864.

EXAMPLE 5

Synthesis, Purification and Conjugation of Peptide P31/47

A synthetic peptide covering the amino acid residues 31 to 47 was synthesized following the stepwise solid-phase strategy as described by Barany and Merrifield (1980) and was purified by reversed-phase high performance liquid chromatography.

Amino acid composition was verified by amino acid analysis. The synthetic peptide was coupled to bovine serum albumin (BSA) with glutaraldehyde according to Geerlings et al (1988).

EXAMPLE 6

Preparation of Recombinant Fusion Proteins

Recombinant fusion proteins consisting of parts of 16 kDa covalently coupled to Schistosoma japonicum gluthatione S-transferase (Smith et al., 1986) were synthesized using the pGEX-2T vector (Smith et al., 1988) in which the appropriate Pfs16 gene fragments (BamHl/DraI, BamHl/SspI fragments, respectively) were inserted. Expression was carried out in E. coli JM101 recA. Fusion proteins were isolated by adsorption and subsequent elution from glutathione agarose beads (Sulphur linkage, Sigma).

EXAMPLE 7

New Zealand rabbits were injected subcutaneously with an homogenate of 200 µg of P31/47 BSA conjugate emulsified in Freund's complete adjuvant, boosted at three-week intervals with P31/47 BSA conjugate in Freund's incomplete adjuvant.

The rabbits were bled from the main ear vein seven days after each boost. Blood was allowed to clot at 4° C. overnight and sera were stored at −20° C. until used.

Antisera from the immunized rabbits were analysed for reactivity against both gametes and gametocytes of P. falciparum by immunoblotting. Gametes and gametocytes extracts were prepared by boiling $1 \times 10^6$ parasites in SDS sample buffer (62.5 mM Tris.Cl, 2% SDS, 10% glycerol, 5% 2-mercaptoethanol, 0.003% bromophenol blue). Polyacrylamide (10%–20%) gels containing SDS (0.1%) were made and run under denaturing conditions according to Laemmli (1970). Proteins were transferred to 0.45 µm nitrocellulose filters as described (Towbin et al., 1979). The nitrocellulose filters were blocked with 1% milkpowder in TBST (50 mM Tris.HCl, 200 mM NaCl, 5 mM EDTA, 0.05% Tween-20, pH 7.5), before incubation with 1:100 dilution of the different rabbit antisera for 1–2 h. Detection was accomplished with 1:8000 dilution of alkaline phosphatase-goat anti rabbit IgG(H+L) in TBST buffer for 1 hour. After extensively washing with RBS the colouring reaction was carried out with 5-bromo-4-chloro-3-indolyl phosphate (p-toluidine salt, Sigma) and Nitroblue-tetrazolium chloride in 100 mM Tris, 100 mM NaCl and 5 mM $MgCl_2$ (pH 9.5). The filters were developed until bands appeared, and then washed in 20 mM Tris.HCl (pH 8.0) and 5 mM EDTA.

The Western blot analysis showed that the antibodies prepared against the synthetic peptide reacted strongly with a protein of Mr=16 kDa in protein extracts of both gametes and gametocytes. The antibodies also reacted with dried gametes and gametocytes in a standard immunofluorescence assay (Moelans et al 1991).

This conclusion was substantiated by immuno-gold electron microscopy studies (see below) using the rabbit antibodies raised against the synthetic peptide. These studies clearly showed that the 16kDa protein is present at the surface of Plasmodium falciparum gametes and gametocytes.

Immunoelectron Microscopy

P. falciparum (NF54) was cultured in a tipper system and synchronized as previously described (Ponnudurai et al., 1986). Blood samples containing gametocytes were taken out of culture and immediately fixed. To initiate exflagellation and detect gametes, other samples were kept for 10 and 30 minutes at room temperature before fixation. All samples were fixed for 2 h in 1% acrolein/2% paraformaldehyde in 0.1M phosphate buffer, centrifugated (1500×g) for 10 minutes and resuspended in 2% (w/v) paraformaldehyde in 0.1M phosphate buffer. After one night at 4° C. the cells were washed extensively in phosphate buffer and the pellet embedded in gelatin (2% w/v). After dehydration to ethanol 70% the samples were embedded in L. R. white resin, medium grade (London Resin Co. Ltd) and polymerized at 50° C. Thin sections were etched for 15 minutes at room temperature in drops of a saturated aqueous solution of sodium metaperiodate, rinsed with distilled water and preincubated with 1% bovine serum albumin in 0.1M phosphate buffer. They were subsequently incubated overnight in a humid chamber at 4° C. on 50 µl drops of the antibody against P31/47 appropriately diluted until a concentration of about 25 µg/ml was achieved. The sections were thoroughly washed and reacted for 1 h with protein A gold (10 mm) (Slot and Geuze, 1985). Control sections were incubated with preimmune sera. After final washing they were postfixed for 10 minutes with 2% glutaraldehyde, washed and stained with uranylacetate.

Western blot analysis of total gametocyte, macrogamete/zygote and sporozoite proteins, using rabbit antiserum raised against the synthetic peptide 31/47, BamHl/DraI fragment, and BamHl/SspI fragment fusion proteins, has also shown that the 16kDa protein is present in protein extracts of *P. falciparum* sporozoites (Moelans et al 1991a). Immuno-gold electron microscopy analysis has confirmed this finding, and located the 16 kDa protein evenly spread on the surface of the sporozoite (Moelans et al 1991). Reaction was obtained with rabbit antisera raised against the synthetic peptide and the BamHl/DraI fusion protein.

EXAMPLE 8
Vaccine Formulations

A vaccine based on the 16 kDa antigen may be designed to achieve one or both of the following aims:

Elicit immunity against the sexual stage parasites by inducing the production of high titres of transmission blocking antibodies.

Elicit protective immunity against the exoerythrocytic stages of the parasite through the production of high titres of neutralizing anti-sporozoite antibodies as well as a strong cell mediated immune response directed toward the liver stage parasite.

An illustrative vaccine of this invention is prepared as follows:

To a buffered, aqueous solution of 3% aluminum hydroxide (10 mM sodium phosphate, 150 mM NaCl, pH6.8; sterilized by filtration), the *P. falciparum* polypeptide of this invention in similar buffer is added with stirring to a final concentration of 100 µg/ml of polypeptide and 0.5 mg/ml of aluminium ($A^{3+}$). The pH is maintained at 6.8. The mixture is left overnight at about 0° C. Thimerosal is added to a final concentration of 0.0005%. The pH is checked and adjusted, if necessary, to 6.8.

The vaccines of the invention may be designed to elicit an antibody response, a cell-mediated response, or a combination of the two. Like the CS protein; the 16 kDa protein of the present invention is present at the surface of sporozoites. It is therefore most probably carried into the hepatocytes by the invading parasite. By analogy with the CS protein, the 16 kDa antigen may therefore be a suitable target for cytotoxic T cells directed towards infected liver cells (Nature, 341, 323–325 (1989)). The techniques which are available for eliciting a cell-mediated response include the following:

(a) Immunization with a live recombinant virus expressing the antigen of interest, as described for example in Science, 224: 397-9 (1984) and Nature, 334,258–260 (1988) for vaccinia, Proc. Natl. Acad. Sci. USA 84,3896–3900 (1987) for varicella-zoster, and Journal of Infectious Diseases 161: 27–30 (1990) for adenovirus.

(b) Immunization with a live recombinant bacterium expressing the antigen of interest, as described for example in Vaccine, 7,495–498 (1989), WO89/02924, Science, 240, 336–338 (1988), and USSN222,202 of SmithKline Beckman (EP-A-0357208) for Salmonella, and in WO90/00594 for mycobacteria such as *Mycobacterium bovis*.

(c) The antigen may be carried by a particle which may or may not itself be immunogenic. For example, Valenzuela et al., (U.S. Pat. No. 4,722,840), EP-A-0278940 and Rutgers et al. (Bio/Technology, 6: 1065–70 (1988)) teach various length *P. falciparum* CS repeats fused to the Hepatitis B surface antigen. The fusions are expressed as viral particles in *Saccharomyces Cerevisiae*.

(d) The antigen may alternatively be carried by inert particles such as liposomes as described in Immunology Today, 11, No. 3 (1990), 89 et seq., or inserted into immunostimulating complexes (ISCOMs) as described in Nature, 308: 457–460 (1984).

References

Barany, G. and Merrified, R. B. (1980) In Gross, E. and Meinhofer, J. (eds.), The Peptide, Vol. 2. Academic Press New York. pg. 3.

Carter, R. Gwadz, R. W. and Mc Auliffe, F. M. (1979) Exp. Parasitol., 47, 185.

Carter, R. Miller, L. H., Rener, J., Kaushal, D., Kumar, N., Graves, P., Grotendorst, P., Gwadz, C., French, R. and Wirth, D. 1984) Phil. Trans R. Soc. Lond., 307, 201–213.

Casadaban, M. J. and Cohen, S. N. (1980) J. Mol. Biol., 138, 179–207.

Gwadz, R. W. (976) Science (Wash. D.C.), 193, 1150–1151.

Geerlings, H. J., Weijer, W. J., Bloemhuff, W., Welling, G. W. and Welling-Wester, S. (1988) J. Immunol. Methods, 106, 239–244.

Gubler, U. and Hoffmann, B. J. (1983) Gene, 25, 263–269.

Kaslow, D. C., Quakyi, I. A., Syin, C., Raum, M. G., Keister, D. G., Coligan, J. E., Mc Cutchan, T. F. and Miller, L. H. (1988) Nature, 333, 74–76.

Kaslow, D. C., Quakyi, I. A. and Keister, D. G. (1989) Molecular and Biochemical Parasitology, 32, 101–104

Kaushal, D. C., Carter, R., Rener, J., Grotendorse, C. A. Miller, L. F. and Howard, R. J. (1983) J. Immunol., 131,2557

Konings, R. (1987) Methods in Enzymology, 153, 12–34.

Laemmli, U. K. (1970) Nature 227, 680–685.

Manniatis, T., Fritsch, E. F. and Sambrook, J. (1982) Molecular Cloning. A Laboratory Manual. Cold Spring Harbor Laboratory Press, Cold Spring Harbor, N.Y.

Miller, L. H. et al. (1986) Science, 234, 1349–1356.

Moelans, I. I. M. D., Meis, J. F. G. M., Kocken, C., Konings, R. N. H., Schoenmaker, J. G. G., Mol. Biochem. Parasit 45 193–204 (1991a).

Nussenzweig, V. and Nussenzweig, R. S. (1989) Advances in Immunology. Academic Press, Inc., Vol.45, pp. 283–334

Panyim, S., Walairat, P. and Yuthavong, Y. (1985) Application of genetic engineering to research on tropical disease pathogens with special reference to Plasmodia. A laboratory manual of selected techniques.

Ponnudurai, T., Lensen, A. H. W. and Meuwissen, J. H. E. Th. (1983) Parasitology, 87, 439.

Quakyi, I. et al. (1987) J. Immunol., 139, 4213–4217

Remaut, E., Stanssens, P. and Fiers, W. (1983) Nucleic Acids Res., 11, 4677–4688.

Rener, J., Graves, P. M., Willams, J. L. and Burkot, T. R. (1983) J. Exp. Med., 158 976.

Sanger, F., Nicklen, S. and Coulson, A. R. (1977) Proc. Natl. Acad. Sci., USA, 74, 5463–5467.

Smith, D. B. Davern, K. M. Board, P. G., Tiu, W. U., Garcia, E. G. and Mitchell, G. F. (1986) Proc. Natl. Acad. Sci. USA, 83, 8703–8707.

Smith, D. B. and Johnson, K. S. (1988) Gene, 67, 31–40.

Towbin, M., Staehekin, T. and Gordon, J. (1979) Proc Natl. Acad. Sci. USA, 76, 4350–4354.

Slot, J. W. and Geuze, H. J. (1985) Eur. J. Cell. Biol., 38, 87–93.

Vermeulen, A. N., Ponnudurai, T., Lensen, A. H. W., Roeffen, W. F. G., Meuwissen, J. H. E. Th (1983) Trans. R. Soc. Trop. Med. Hyg. 77, 753–759.

Vermeulen, A. N., Ponnudurai, T., Beckers, P. J. A., Verhave, J. P., Smits, M. A. and Meuwissen, J. H. E. Th. (1985) J. Exp. Med., 162, 1460–1476.

Vialard, J., Lalumiere, M., Vernet, L., Briedis, D., Alkhatib, G., Henning, D., Levin, D. and Richardson, C., (1990). J of Virology 64 37–50.

Weber, J. L. (1987) Gene, 52, 103–109.
Wesseling, J. G., Dirks, R. Smits, M. A. and Schoenmakers, J. G. G. (1989) Gene, 83, 301–309.

We claim:

1. An isolated DNA sequence encoding the amino acid sequence shown in SEQ ID NO: 2.

2. The isolated DNA sequence of claim 1 as shown in SEQ ID NO: 1.

3. An expression vector comprising the DNA sequence of claim 1.

4. An expression vector comprising the DNA sequence of claim 2.

5. A host cell transformed with the expression vector of claim 3.

6. A host cell transformed with the expression vector of claim 4.

7. An isolated DNA sequence encoding amino acid residues 31–47 of SEQ ID NO: 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 634 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: PLASMODIUM
        ( B ) STRAIN: FALCIPARUM ( v i i ) IMMEDIATE SOURCE:
        ( B ) CLONE: 16K ( x i ) SEQUENCE DESCRIPTION: SEQ ID NO:1:

```
TTTTTATTTT ATTTTTTTA TTTTTTATTT TTTTTTCTTT TGCCATTTTT CTATTTATAC      60
TTTCTTCAAC ATGAATATTC GAAAGTTCAT ACCATCTTTA GCTTAATGC TTATATTCTT     120
CGCTTTTGCA AACCTGGTAT TATCAGATGC AAATGACAAA GCAAAAAAGC CCGCTGGAAA    180
AGGATCCCCT TCAACTTTGC AAACCCCAGG AAGTTCTTCA GGTGCCTCTC TTCATGCTGT    240
TGGACCTAAT CAAGGTGGAC TATCTCAAGG TCTTTCTGGA AAAGATTCTG CTGACAAAAT    300
GCCTTTAGAA ACTCAGCTAG CTATAGAAGA AATCAAGAGC TTATCCAATA TGTTAGATAA    360
AAAAACGACA GTTAACAGAA ACTTAATCAT AAGTACTGCT GTCACAAATA TGATCATGTT    420
GATCATATTA TCTGGTATAG TTGGATTTAA AGTTAAAAAA ACGAAGAACG CAGATGATGA    480
TAAAGGAGAT AAGGATAAGG ACAAGGATAA TACAGATGAA GGAGACGAAG GAGATGATTC    540
TTAAATGTAT ATATATATAT ATATATATAT ATTTATTTAT TTATTTAAAT ATTTATATAT    600
ATATATATAT TATATATATA ATATTTATA ATTT                                 634
```

( 2 ) INFORMATION FOR SEQ ID NO:2:

( i ) SEQUENCE CHARACTERISTICS:
        ( A ) LENGTH: 157 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: PLASMODIUM
        ( B ) STRAIN: FALCIPARUM ( v i i ) IMMEDIATE SOURCE:
        ( B ) CLONE: 16K ( x i ) SEQUENCE DESCRIPTION: SEQ ID NO:2:

```
Met Asn Ile Arg Lys Phe Ile Pro Ser Leu Ala Leu Met Leu Ile Phe
1               5                   10                  15

Phe Ala Phe Ala Asn Leu Val Leu Ser Asp Ala Asn Asp Lys Ala Lys
                20                  25                  30

Lys Pro Ala Gly Lys Gly Ser Pro Ser Thr Leu Gln Thr Pro Gly Ser
            35                  40                  45

Ser Ser Gly Ala Ser Leu His Ala Val Gly Pro Asn Gln Gly Gly Leu
    50                  55                      60

Ser Gln Gly Leu Ser Gly Lys Asp Ser Ala Asp Lys Met Pro Leu Glu
65                  70                  75                      80

Thr Gln Leu Ala Ile Glu Glu Ile Lys Ser Leu Ser Asn Met Leu Asp
                85                  90                      95

Lys Lys Thr Thr Val Asn Arg Asn Leu Ile Ile Ser Thr Ala Val Thr
            100                 105                 110

Asn Met Ile Met Leu Ile Ile Leu Ser Gly Ile Val Gly Phe Lys Val
            115                 120                 125

Lys Lys Thr Lys Asn Ala Asp Asp Asp Lys Gly Asp Lys Asp Lys Asp
    130                 135                 140

Lys Asp Asn Thr Asp Glu Gly Asp Glu Gly Asp Asp Ser
145                 150                 155
```